(12) United States Patent
Griswold

(10) Patent No.: US 6,375,652 B1
(45) Date of Patent: Apr. 23, 2002

(54) CUTANEOUS CRYOSURGICAL CLAMP

(75) Inventor: Thomas A. Griswold, Ellington, CT (US)

(73) Assignee: Brymill Corporation, Ellington, CT (US)

( * ) Notice: Subject to any disclaimer, the term of this patent is extended or adjusted under 35 U.S.C. 154(b) by 0 days.

(21) Appl. No.: 09/564,968

(22) Filed: May 4, 2000

(51) Int. Cl.$^7$ ................................................ A61B 18/18
(52) U.S. Cl. ....................................................... 606/20
(58) Field of Search ............................. 606/20, 21, 22, 606/23, 24, 25, 26, 51, 52

(56) References Cited

U.S. PATENT DOCUMENTS 5,733,280 A  *  3/1998  Avitall ........................ 606/23

* cited by examiner

Primary Examiner—R Kearney
(74) Attorney, Agent, or Firm—M. P. Williams

(57) ABSTRACT

A cutaneous clamp 8 has angled, hollow tubes 23, 24 leading to hollow jaws 27, 28 having vents 30, 31, with a spacer 40 which can force the tubes together so that the jaws close upon tissue when the spacer is moved along the tubes by operator controlled means 41, 42. The clamp is removably fastened to a source 7 of cryogenic fluid which flows through the tubes and jaws and out the vents 30, 31 and related tubing 33–38.

4 Claims, 2 Drawing Sheets

CUTANEOUS CRYOSURGICAL CLAMP

TECHNICAL FIELD

This invention relates to a cryosurgical clamp particularly adapted for necrotizing cutaneous lesions cryosurgically.

BACKGROUND ART

The presence of acrochordon (also called "papillomatous cutaneous lesions", "cutaneous tags", or "skin tags") is quite common in persons who are at least middle aged. For simplicity, reference will be had to "skin tags" herein. When skin tags are relatively new, they respond quite well to medication, such as steroid-based creams or ointments. However, when skin tags have matured for many months or years, the response to medication is less satisfactory. For this reason, it has been known to use various surgical methods to excise tags, including knife surgery, cautery and cryosurgery. In the past, hemostat-type clamps have been adapted to be cooled with cryogenic gases or liquids, and utilized to necrotize cutaneous lesions. However, in most instances, one hand of the surgeon is required to position and manipulate the lesion which is to be necrotized, either with his fingers or with a tweezer or clamp, while the other hand is utilized to manipulate the cryosurgical instrument in use. Cryosurgical clamps known to the prior art do not lend themselves for single-handed use, since typically one hand is required to support and manipulate the cryogen source, and another hand is required to manipulate the clamp itself. Another problem with prior cryosurgical clamps is that the mating surfaces of the jaws are rather wide, thereby precluding a narrow, sharp surgical margin.

DISCLOSURE OF INVENTION

Objects of the invention include provision of a cutaneous cryosurgical clamp which is easily operated, along with the cryogenic source, with one hand; and a cryosurgical clamp which provides a very sharp surgical margin.

According to the present invention, a cutaneous cryosurgical clamp which utilizes a hand-held cryosurgical instrument as a source comprises mating clamp jaws, each jaw mounted on and fed cryogenic fluid by a corresponding feed tube, the two feed tubes being non-parallel with respect to each other and joined by a spacer which when drawn toward the user will bring the jaws of the clamp together for use. In accordance further with the invention, the jaws are chisel shaped, thereby providing for a sharp surgical margin parallel with a general skin surface upon which a lesion to be necrotized has grown.

The clamp of the invention is easy to use, and has no working parts that are subject to becoming frozen (and therefore inoperable), as a consequence of the very low temperatures attendant its use.

Other objects, features and advantages of the present invention will become more apparent in the light of the following detailed description of exemplary embodiments thereof, as illustrated in the accompanying drawing.

BEST MODE FOR CARRYING OUT THE INVENTION

Figure 1:
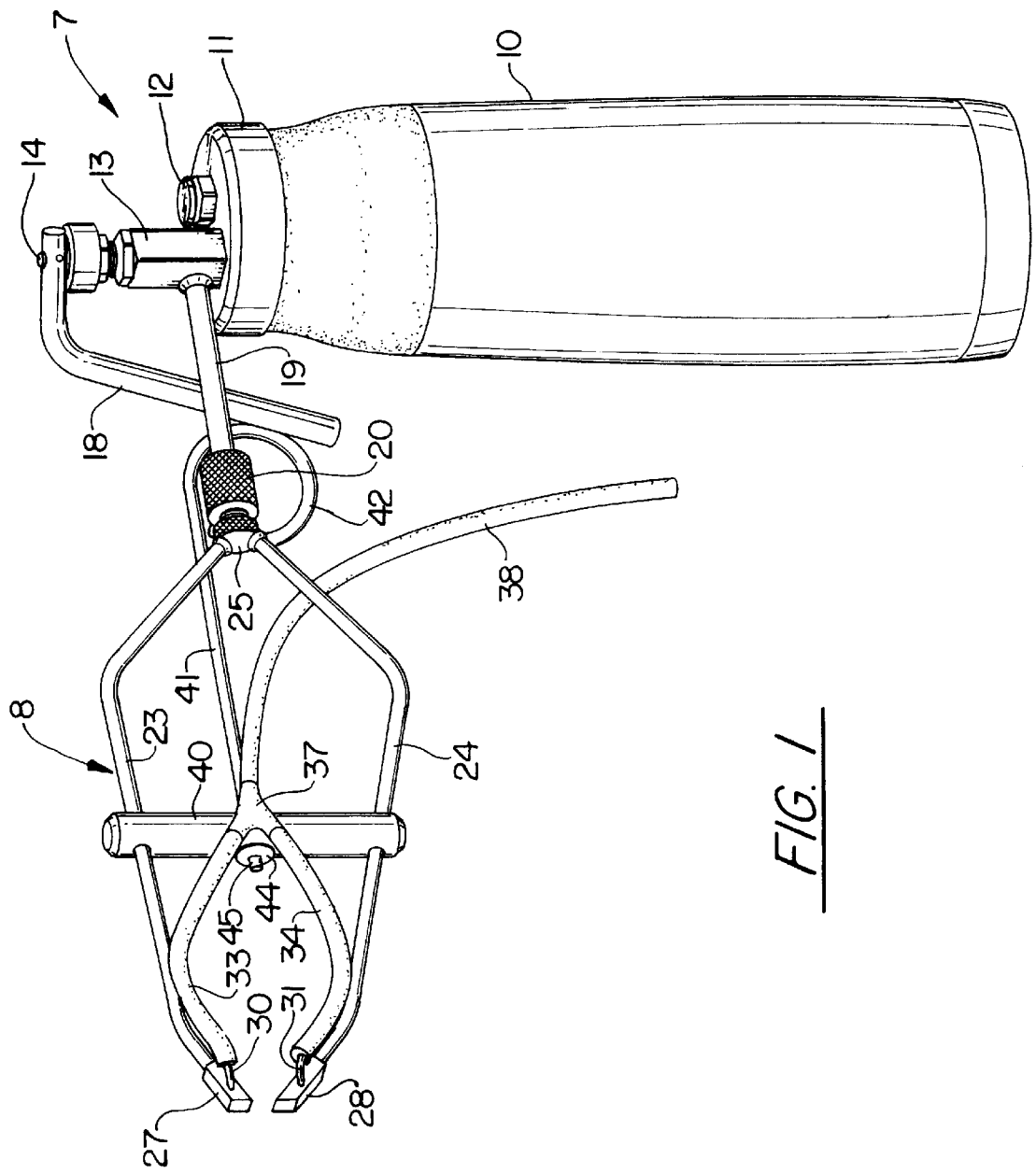
FIG. 1 is a perspective view of the inventive clamp with the jaws open, attached to a cryosurgical instrument with its cryogen delivery valve closed.

Referring to FIG. 1, a cryosurgical instrument 7 of the type disclosed in U.S. Pat. No. 5,947,960 is shown fitted with a cutaneous cryosurgical clamp 8 of the invention. The instrument 7 includes a dewar 10 having a threaded cap 1 1 upon which is mounted a safety valve 12 and a flow valve disposed within a housing 13. The flow valve is operated by lifting a stem 14 as a result of drawing a trigger bar 18 toward the unit 7. The unit 7 has a nitrogen delivery tube 1 9 which terminates in a knurled fitting 20, that permits having various spray apertures, closed probes and other accessories attached thereto. The clamp 8 comprises a pair of shaped, hollow tubes 23, 24 that are brazed or otherwise bonded to a blind tip 25 which has threads complementary to the internal threads of the knurled fitting 20. Nitrogen flowing through the delivery tube 19 will enter the blind tip 25 and then pass through each of the tubes 23, 24. The tubes 23, 24 have hollow jaw pieces brazed or otherwise bonded to their distal ends, the hollow jaw pieces 27, 28 in turn having small exhaust tubes 30, 31 bonded to and in fluid communication with the interior of the hollow jaws 27, 28. As the nitrogen flows into the hollow jaws 27, 28 it impinges on the walls thereof and vaporizes, the heat of vaporization causing extreme chilling (down to nearly −476°F.), the gas passing through the exhaust tubes 30, 31 and into plastic tubing 33, 34. The tubing 33, 34 is joined by a hollow Y-shaped piece 37 to an additional length of tubing 38 that directs the effluent cold gas away from the surgeon and the surgical field.

The tubes 23, 24 each pass through a spacer 40 that will generally position itself in the manner shown so that the jaw pieces 27, 28 are separated. Passing loosely through the spacer 40 is a rod 41 having a proximal end turned into a circle 42 so that it can be engaged by the finger of a user. The distal end of the rod 41 fits loosely through the spacer 40, and is fitted with a washer 44, held on by crimping 45 or in any other suitable way.

Figure 2:
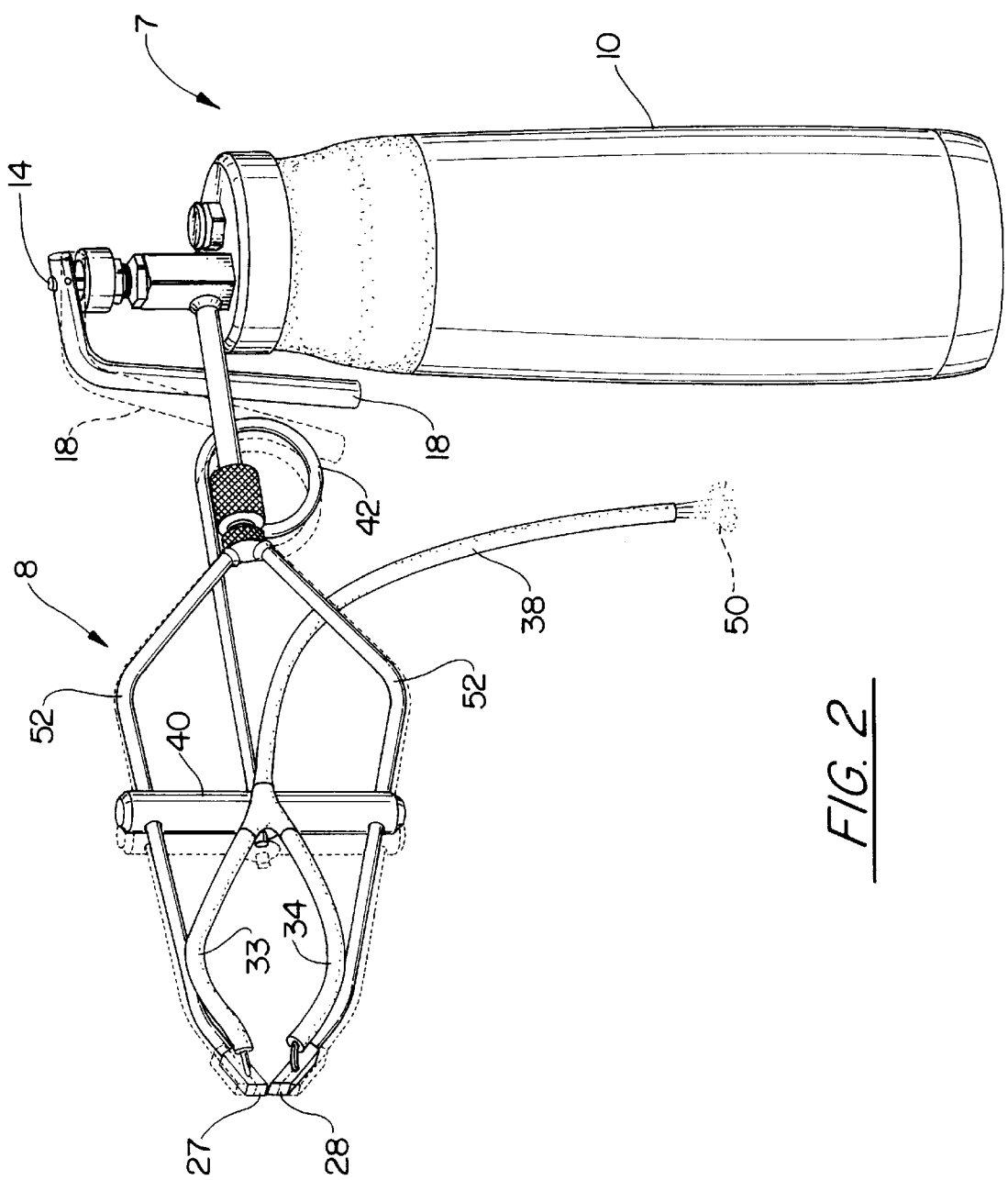
FIG. 2 is a perspective view of the inventive clamp with the jaws in the closed, operative position, and the cryosurgical instrument having its valve in the cryogen delivery position.

In FIG. 2, the trigger bar 18 has been moved toward the unit 7 thereby raising the valve stem 14 and allowing nitrogen to flow out of the container 10 through the delivery tube 19 and the blind cap 25, into the tubes 23, 24. Gaseous nitrogen is then vented through the tubes 33, 34, 38 to atmosphere, as at 50. With the finger inserted in the circle 42, the user draws the circle 42 toward the instrument 8, the rod 41 will pull on the spacer 44 so that the spacer 44 slides along the tubes 23, 24, to the right as seen in FIG. 2, thereby drawing the tubes 23, 24, and hence the jaws pieces 27, 28, closer together. The rod 41 may be fitted with another washer (not shown) on the proximal side of the spacer 40, so that pushing the ring 42 away from the instrument 7 will force the jaws 27, 28 to become open, at the conclusion of a procedure.

In use, the physician will generally engage a piece of cutaneous tissue which is to be removed, either with his fingers or by means of tweezers or a clamp. With the tissue extended outwardly from the surface of the skin, the physician generally will operate the valve trigger bar 18 so as to begin to circulate cryogenic fluid through the clamp. When the jaw pieces 27, 28 are very cold, then the physician will pull the ring 42 toward the unit 7, thereby causing the jaws to close over the tissue as seen in FIG. 2.

The spacer 40 may, for instance, be ⅜ inch diameter Delrin about two inches long. The tubes 23, 24 may be one-eighth inch hard stainless steel tubing, the overall length of each piece being just under six inches. The exhaust tubes 30, 31 may be one-sixteenth stainless tubing about one inch long; they may extend from the sides of the jaw pieces 27, 28 at about a 45° angle so as to facilitate leading the tubing 33, 34, 38 away from the surgical field. The jaw pieces 27, 28 may comprise three-sixteenths square brass stock, about one-half inch long.

If desired, the spacer 40 could be disposed on the instrument side of the bends 52 in the tubes 23, 24 so that pushing on the ring 42 would cause the jaws to close. However, that action appears to be more difficult to accomplish, so the form of the apparatus shown is to be preferred. In this embodiment, the operator controlled means for drawing the separator 40 toward the fitting 25 is the rod 41 with the circle 42 formed therein. However, the rod could have other shapes. The spacer 8 could be attached to the trigger bar 1 8, once the clamp 8 is installed on the instrument 7; however, it is believed to be preferable to keep them separate so that the jaws can be chilled before being applied to tissue. The tubes 30, 31 and/or tubing 33, 34, 38 may be eliminated, if desired, so long as cold gas is not directed toward the patient or the physician; however, it is believed to be preferable to use the tubing fitted onto the tubes. The jaws 27, 28 could have other shapes, although the chisel shape shown is preferred.

The aforementioned patent is incorporated herein by reference.

Thus, although the invention has been shown and described with respect to exemplary embodiments thereof, it should be understood by those skilled in the art that the foregoing and various other changes, omissions and additions may be made therein and thereto, without departing from the spirit and scope of the invention.

I claim:

1. A cutaneous cryosurgical clamp comprising:
   a fitting having a proximal portion adapted to be connected to a source of liquified cryogenic gas and having a face distal of said proximal portion;
   a pair of rigid tubes, a proximal end of each of said tubes being affixed to and in fluid communication with said fitting, each of said tubes extending outwardly from said face at an angle,
   each of said tubes having a bend, a proximal segment of each tube being between said face and said bend, successively distal incremental portions of length of said tubes in said proximal segment being separated from each other by successively larger amounts, each tube having a segment distal said bend, successively distal incremental portions of said tubes in said distal segment being progressively closer to each other;
   a pair of hollow jaw pieces, one affixed to and in fluid communication with a distal end of each of said tubes, each of said jaw pieces having a vent to allow passage of cryogenic fluid therefrom;
   a separator having holes through each end thereof, the distal segment of each one of said tubes passing through a corresponding one of said holes, the distal ends of said tubes, when said tubes are in a relaxed state, being spread sufficiently so that said jaw pieces do not contact each other; and
   operator controlled means for moving said separator along said tubes in a direction to force the distal ends of said tubes close enough together so that said jaw pieces will close upon any tissue which may be therebetween.

2. A clamp according to claim 1 wherein each of said jaw pieces has a chisel shape, having an edge perpendicular to a major plane of said clamp.

3. A clamp according to claim 1 further comprising:
   tubing connected with the vent of each of said jaw pieces, to lead cryogenic fluid away from said jaw pieces.

4. A clamp according to claim 1 wherein said separator is disposed distal of said bends, said means drawing said separator toward said fitting.

* * * * *